United States Patent
Flohr

(10) Patent No.: US 7,555,095 B2
(45) Date of Patent: Jun. 30, 2009

(54) METHOD FOR RECORDING AND PRODUCING A TOPOGRAM

(75) Inventor: Thomas Flohr, Uehlfeld (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/976,806

(22) Filed: Oct. 29, 2007

(65) Prior Publication Data

US 2008/0123801 A1 May 29, 2008

(30) Foreign Application Priority Data

Oct. 30, 2006 (DE) .................... 10 2006 051 147

(51) Int. Cl.
*A61B 6/03* (2006.01)

(52) U.S. Cl. ............................................. 378/4; 378/19

(58) Field of Classification Search .............. 378/4–27; 99/4–20
See application file for complete search history.

(56) References Cited

U.S. PATENT DOCUMENTS

| 6,421,412 | B1 * | 7/2002 | Hsieh et al. | ..................... 378/9 |
| 7,302,030 | B2 * | 11/2007 | Bruder et al. | .................. 378/9 |
| 2005/0232390 | A1 | 10/2005 | Bruder et al. | |

FOREIGN PATENT DOCUMENTS

DE 10 2004 017 538 A1 4/2004

* cited by examiner

*Primary Examiner*—Hoon Song
(74) *Attorney, Agent, or Firm*—Harness, Dickey & Pierce, P.L.C

(57) ABSTRACT

A method is disclosed for recording a topogram data record for producing a topogram using an X-ray computer tomograph. To improve the image quality of the topogram, it is proposed that the topogram data record be recorded using a spring focus parallel and/or in azimuth with respect to a system axis of the X-ray computer tomograph.

13 Claims, 2 Drawing Sheets

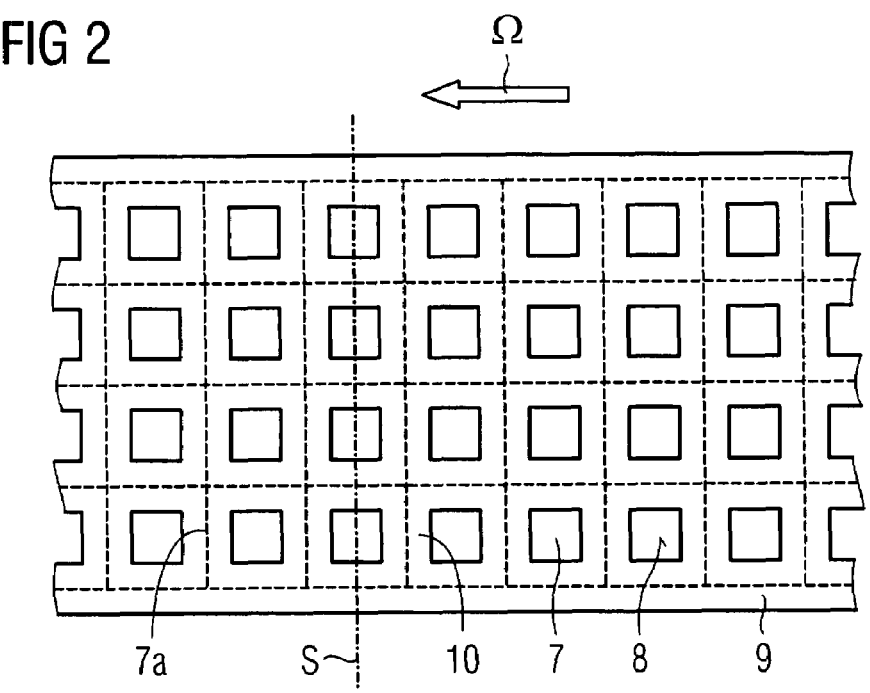
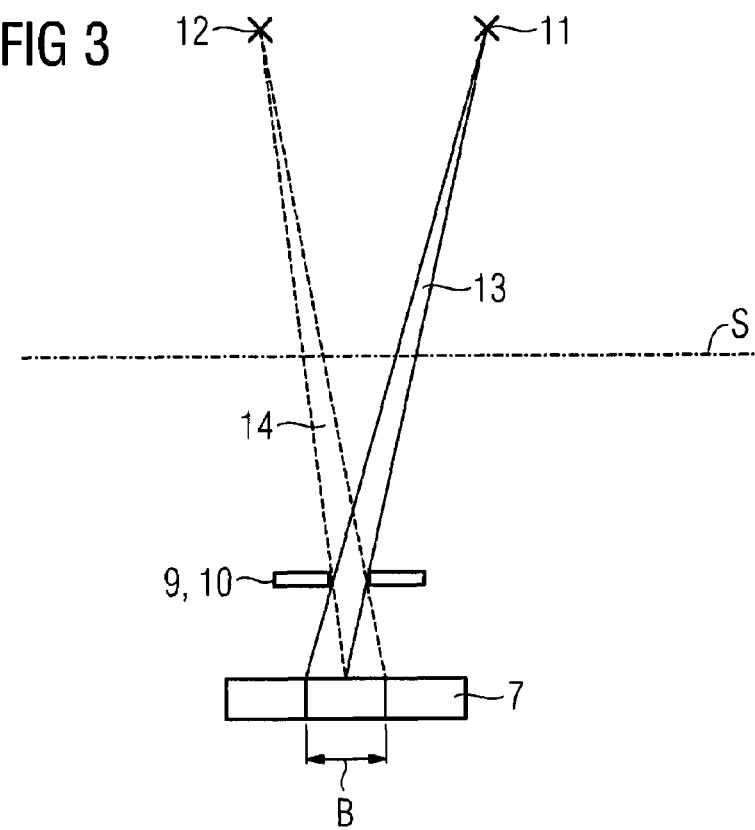

METHOD FOR RECORDING AND PRODUCING A TOPOGRAM

PRIORITY STATEMENT

The present application hereby claims priority under 35 U.S.C. §119 on German patent application number DE 10 2006 051 147.6 filed Oct. 30, 2006, the entire contents of which is hereby incorporated herein by reference.

FIELD

Embodiments of the invention generally relate to a method for recording a topogram data record for producing a topogram.

BACKGROUND

For computer tomograph examinations, a desired examination region of a body which is to be examined is usually found and selected by producing a general scan—also called a topogram. The topogram is a parallel or central projection of the body which reproduces the anatomic structure of the body. On the basis of the topogram, it is possible to stipulate a start and end point for, by way of example, layered scanning of the desired examination region.

For computer tomograph examinations, an X-ray detector unit in an X-ray computer tomograph is normally rotated about a system axis. When recording the topogram, on the other hand, the X-ray detector unit is static relative to the system axis, with the body being moved along the system axis when the topogram data record is recorded.

The topogram opens up the option of simple anatomic orientation. Although the topogram is not provided for diagnostic purposes, it would be desirable for certain areas of application if the topogram had diagnostic image quality. By way of example, it would be desirable when examining an emergency patient if the topogram could be taken as a basis for performing early diagnosis of any fractures, particularly of the spine, and internal injuries. This would render superfluous firstly early assessment of the patient's state of health, and secondly conventional X-ray scans. It would be possible, inter alia, to significantly reduce a dosage for the patient which is conditional on multiple X-ray examinations.

SUMMARY

In at least one embodiment, the present invention provides a method for recording a data record for producing a topogram having diagnostic image quality. In other embodiments, an X-ray computer tomograph, a computer program and a storage medium are provided which allow performance of a method for recording and producing a topogram having diagnostic image quality.

In at least one embodiment, the invention provides a method for recording a topogram data record for producing a topogram using an X-ray computer tomograph. In at least one embodiment of the method, the topogram data record is recorded using a spring focus parallel and/or in azimuth with respect to a system axis of the X-ray computer tomograph.

A spring focus allows the periodic use of a plurality of focus positions, spaced apart from one another parallel and/or in azimuth with respect to the system axis, during the recording in at least one embodiment. It is therefore possible to record absorption data for a plurality of projection directions which are slightly different than one another. This allows the resolution or image quality of the topogram to be improved such that a diagnosis can be made directly on the basis of the topogram. A spring focus is implemented in the X-ray computer tomograph of type "SOMATOM 40/64" from Siemens AG, for example.

According to one refinement of at least one embodiment of the method, the topogram data record is recorded using a detector which has a multiplicity of detector elements arranged in the manner of a matrix. In this case, the beam path of the X-ray radiation between the object and the detector contains a bar grid. The bar grid has grid bars which are essentially nontransparent to the X-ray radiation. Thus, the bar grid essentially fully absorbs the X-ray radiation hitting it.

The bar grid is provided such that an aperture in the detector elements is reduced parallel and/or in azimuth with respect to the system axis. A reduction in the aperture in combination with the spring focus advantageously allows the resolution and hence the image quality to be increased such that the topogram allows a diagnosis directly. By way of example, it is possible to improve the resolution of the topogram from 6 line pairs per cm (1 p/cm) to greater than 15 1 p/cm. Such a resolution is sufficient to be able to produce at least preliminary diagnoses or findings about anatomic anomalies, for example. Apart from this, the effect which can be achieved with the spring focus is that the dosage for a patient is at least not substantially higher in comparison with conventional methods for recording a topogram.

Within the context of this disclosure, the term aperture is understood to mean an opening in an effective radiation intake face of the detector elements for the X-ray radiation.

According to another refinement of an embodiment, the grid bars and corresponding grid meshes of the bar grid are in a form such that the aperture is reduced by no more than half parallel and/or in azimuth with respect to the system axis. The grid bars and grid meshes can be in a form and arranged, and focus positions of the spring focus can be stipulated, such that successive measured values from each detector element can be recorded parallel and/or in azimuth with respect to the system axis using half a channel width defined by the aperture parallel or in azimuth with respect to the system axis. In this case, an effective channel width may have been shifted by half the total channel width for successive measurements parallel and/or in azimuth with respect to the system axis. This firstly allows topograms having diagnostic image quality to be produced.

In at least one embodiment, the invention also provides a further method for producing a topogram of at least one subregion of an object using an X-ray computer tomograph comprising:

a) a topogram data record is recorded in line with the inventive method or one of its refinements, and b) the topogram is produced on the basis of the topogram data record.

In at least one embodiment, the invention also provides a computer program, comprising a computer-readable program code which, when executed on a computer associated with an X-ray computer tomograph, prompts the inventive method or one of its refinements. It also provides an X-ray computer tomograph having a computer and also a storage medium which has stored the computer program. As far as the advantageous effects of the further method, the computer program, the X-ray computer tomograph and the storage medium are concerned, reference is made to the preceding comments relating to the inventive method and its refinements.

BRIEF DESCRIPTION OF THE DRAWINGS

The invention is described below with the aid of example embodiments. In the drawings:

FIG. 2 schematically shows a plan view of a section of a detector with a bar grid, and FIG. 3 schematically shows a topogram data record being recorded by means of a spring focus using the detector with the bar grid shown in FIG. 2.

DETAILED DESCRIPTION OF THE EXAMPLE EMBODIMENTS

Figure 1:
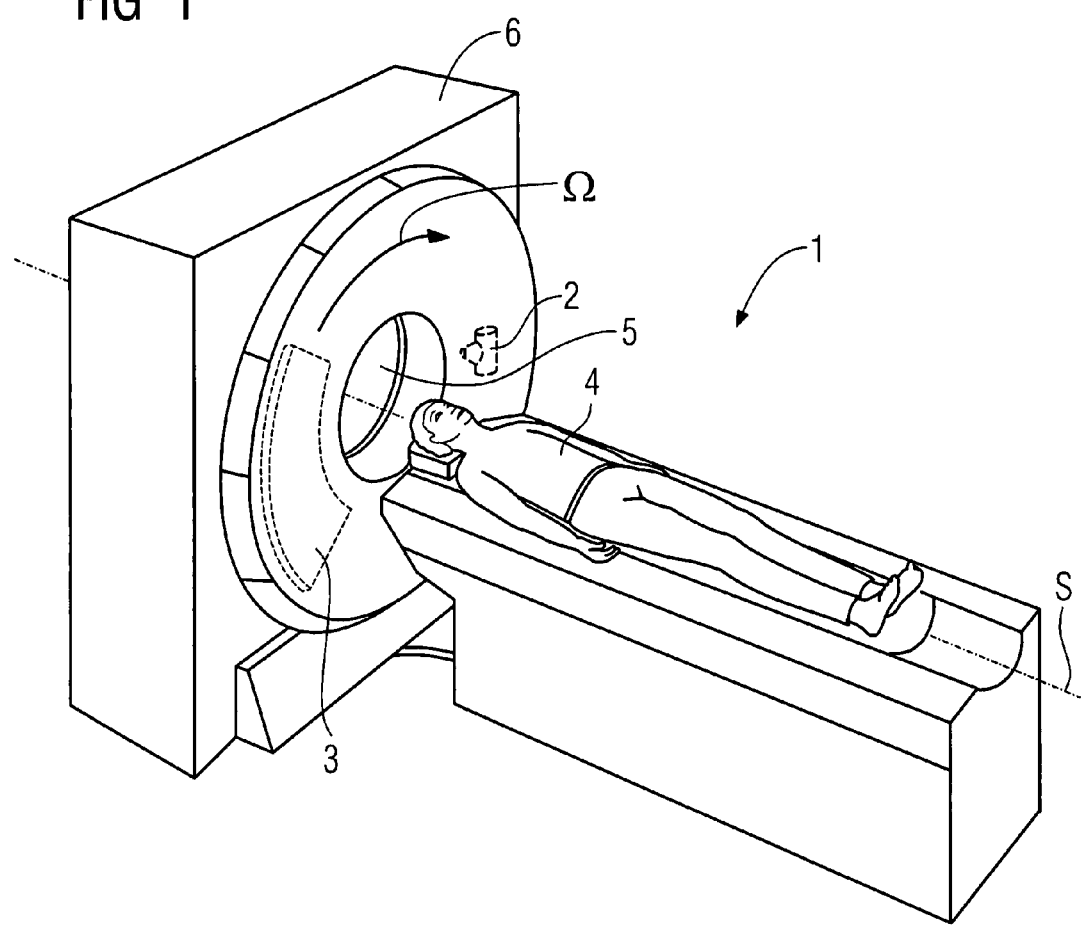
FIG. 1 schematically shows an X-ray computer tomograph.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items. In the figures, elements which are the same or have the same function are denoted by the same reference symbols throughout. The figures are not true to scale, and scales for the individual figures may differ from one another.

FIG. 1 schematically shows an embodiment of an X-ray computer tomograph 1. The X-ray computer tomograph 1 has an X-ray detector unit with an X-ray tube 2 and a detector 3. The X-ray detector unit can be rotated about a system axis S. A patient 4 accommodated on a couch can be moved into and out of an opening 5, formed between the X-ray tube 2 and the detector 3, in a gantry 6 of the X-ray computer tomograph 1 parallel to the system axis S for the purpose of the computer tomograph examination. An azimuth direction is denoted by the reference symbol $\Omega$. The X-ray computer tomograph has a computer (not shown) for processing recording data and for controlling the X-ray computer tomograph.

FIG. 2 shows a detailed plan view of a section of the detector 3. The detector 3 has a multiplicity of detector elements 7 with respective radiation intake faces 8. In plan view, a bar grid which is essentially impervious to X-ray radiation is arranged above the radiation intake faces 8. To assist the clarity of the illustration, septa 7a formed between the detector elements 7 are shown in dashed lines. The bar grid in the illustration in FIG. 2 has horizontally and vertically running bars 9 and 10, which are subsequently also referred to as bars for the sake of simplicity. The bars are each arranged centrally over the septa 7a and respectively cover the edges of the radiation intake faces 8 such that an aperture defined by the radiation intake face 8 of each detector element 7 is reduced to half both parallel to the direction of the system axis S and in the azimuth direction $\Omega$.

FIG. 3 schematically shows a topogram data record being recorded by way of a spring focus using the detector 3 with the bar grid. For recording using a spring focus, a first and a second focus position 11 and 12 are used in succession in the direction of the system axis S during the recording. The first focus position 11 and the second focus position 12 emit appropriate first 13 and second 14 X-ray radiation during the recording. It must be noted that the spacing between the first or second focus position 11, 12 and the detector 3 is actually much larger than can be seen in FIG. 3. In particular, the spacing between the first focus position 11 and the second focus position thus can be much smaller than shown in FIG. 3, and the first and second X-ray radiation hits the detector element 7 at a much shallower angle. In the azimuth direction $\Omega$, two further focus positions (not denoted or shown in FIG. 3) are provided in similar fashion. The bars 9, 10 are in a form and arranged over the detector elements 7, i.e. septa 7a, and the first and second focus positions 11 and 12 are stipulated, such that successive measurements are taken using an effective channel width which corresponds to a half channel width B defined by the aperture parallel to the system axis S. The same applies to a channel width in the azimuth direction $\Omega$.

FIG. 3, in particular, shows that combining the bar grid with the spring focus allows an improvement in the resolution, and hence the image quality. It is possible to achieve an image quality for the topogram which allows diagnoses to be produced. The image quality can naturally also be improved without a bar grid. In comparison with topogram data records recorded in conventional fashion, in this case the image quality can be significantly improved on the basis of the different focus positions, so that diagnostic statements are possible directly from the topogram.

Finally, it should also be mentioned that the topogram can be recorded by performing the following steps:

the patient 4 is positioned on the couch, the first and second X-ray radiation 13 and 14 is periodically emitted using the spring focus, with the first and/or second focus position(s) 11 and/or 12 parallel and/or in azimuth with respect to the system axis S being periodically used or adopted, the topogram data record is recorded by detecting the X-ray radiation transmitted through the body of the patient 4 using the detector 3, with at least one relevant subregion of the patient 4 being moved between the X-ray detector unit along the system axis S, and with the X-ray detector unit remaining static relative to the system axis, i.e. at the same angle of azimuth, and the topogram is produced on the basis of the topogram data record.

A topogram recorded and produced in this way allows anatomic anomalies to be diagnosed.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDS; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for recording a topogram data record for producing a topogram using an X-ray computer tomograph, comprising:

recording the topogram data record using a spring focus at least one of in parallel and in azimuth with respect to a system axis of the X-ray computer tomography, wherein the topogram data record is recorded using a detector including a multiplicity of detector elements arranged in a matrix, wherein a beam path of X-ray radiation between an object and the detector contains a bar grid whose grid bars are essentially nontransparent to the X-ray radiation, such that an aperture in the detector elements is reduced at least one of in parallel and in azimuth with respect to the system axis.

2. The method as claimed in claim 1, wherein the grid bars and corresponding grid meshes of the bar grid are in a form such that an aperture is reduced by no more than half at least one of parallel and in azimuth with respect to the system axis.

3. The method as claimed in claim 2, wherein the grid bars and grid meshes are in a form and arranged, and focus positions of the spring focus are stipulated, such that successive measured values from each detector element are recordable at least one of parallel and in azimuth with respect to the system axis using half a channel width defined by the aperture at least one of parallel and in azimuth with respect to the system axis.

4. The method of claim 1, further comprising:

producing the topogram for at least one subregion of the object using the X-ray computer tomograph based upon the recorded topogram data record.

5. A computer readable medium encoded with a computer program, which when executed on a computer associated with the X-ray computer tomograph, causes the computer to execute instructions implementing the method of claim 1.

6. An X-ray computer tomograph, comprising:

a computer unit including a computer on which the computer program as claimed in claim 5 is stored.

7. A storage medium comprising a computer program as claimed in claim 5, stored thereon.

8. The method as claimed in claim 1, wherein the grid bars and grid meshes are in a form and arranged, and focus positions of the spring focus are stipulated, such that successive measured values from each detector element are recordable at least one of parallel and in azimuth with respect to the system axis using half a channel width defined by an aperture at least one of parallel and in azimuth with respect to the system axis.

9. A computer readable medium encoded with a computer program, which when executed on a computer associated with the X-ray computer tomograph, causes the computer to execute instructions implementing the method of claim 4.

10. An X-ray computer tomograph, comprising:

a computer unit including a computer on which the computer program as claimed in claim 9 is stored.

11. A storage medium comprising a computer program as claimed in claim 9 stored thereon.

12. A computer readable medium including program segments for, when executed on a computer device associated with the X-ray computer tomograph, causing the computer device to implement the method of claim 1.

13. A computer readable medium including program segments for, when executed on a computer device associated with the X-ray computer tomograph, causing the computer device to implement the method of claim 4.

* * * * *